United States Patent [19]

Peters et al.

[11] Patent Number: Plant 5,587

[45] Date of Patent: Dec. 3, 1985

[54] NECTARINE TREE, "MIKE'S GRAND"

[76] Inventors: Richard Peters, 4854 E. Butler Ave.; Eric Wuhl, 5480 E. Lane St., both of Fresno, Calif. 93727

[21] Appl. No.: 585,272

[22] Filed: Mar. 1, 1984

[51] Int. Cl.[4] ..... A01H 5/03

[52] U.S. Cl. ..... Plt./41

[58] Field of Search ..... Plt./41

*Primary Examiner*—Robert E. Bagwill
*Attorney, Agent, or Firm*—Worrel & Worrel

[57] ABSTRACT

A nectarine tree which very heavily and regularly bears fruit having yellow, semi-freestone flesh and red skin, and which ripens early in the season.

1 Drawing Figure

BACKGROUND OF THE NEW VARIETY

The present invention relates to a new and distinct variety of nectarine tree, denominated by the varietal name "MIKE'S GRAND", and more particularly to such a nectarine tree that is broadly similar to the Star Brite Nectarine Tree (as yet unpatented), but from which it is distinguished by its bearing of fruit having a deeper suture with flesh adhering to its stone on both sutures and having more abundant, coarser fibers.

The subject variety is also closely similar to the May Grand Nectarine Tree (U.S. Plant Pat. No. 2,794) but is distinguished therefrom by its fruit which has flesh more yellow in color and skin somewhat less bright in color, the fruit having a somewhat flatter configuration and ripening two to three days earlier than that of the May Grand.

ORIGIN AND ASEXUAL REPRODUCTION OF THE NEW VARIETY

The subject variety was discovered by us growing in an orchard which we farmed on the East Side Ranch at 16405 East Goodfellow, in the City of Sanger, in the County of Fresno, in the State of Calif. It was found as a single branch growing in an orchard of Early Sungrand Nectarine Trees (unpatented) owned by a partnership comprised of the applicant Richard Peters and CLW and Associates, a New Jersey Corporation. The new variety was asexually reproduced by budding under our supervision and at our instructions at the Bright's Nursery in Le Grand, Calif. Fruit and tree characteristics resulting from this budding proved identical to those of the original sport.

SUMMARY OF THE NEW VARIETY

The instant variety of nectarine tree is characterized by perpetuating the general characteristics of the May Grand Nectarine Tree (U.S. Plant Pat. No. 2,794) in its bearing of early-ripening, semi-freestone fruit, but is distinguished therefrom as to novelty by its greater productivity of fruit having a somewhat flatter shape and which ripens two or three days earlier than that of the May Grand.

The new nectarine tree bears fruit maturing in early June, whose skin attains a color of Maroon (Plate 7-L-7) on a ground color of Doubloom or Roman Ochre (Plate 11-K-10) and whose semi-freestone flesh attains a color of Spanish Yellow (Plate 10-L-7) and has firm, meaty texture with abundant, coarse fibers.

BRIEF DESCRIPTION OF THE DRAWING

The accompanying drawing is a color photograph of four mature nectarines of the subject variety with one of the fruits divided along the suture plane to show the flesh color and stone characteristics, together with a representative twig bearing characteristic leaves.

DETAILED DESCRIPTION

Referring more specifically to the pomological details of the new and distinct variety of nectarine tree, the following has been observed under the ecological conditions prevailing in the designated orchard in Fresno County, Calif. All color code plate identifications are by reference to the A. Maerz and M. Paul *Dictionary of Color,* Second Edition, 1950.

TREE

Size: Large.
Figure: Spreading.
Productivity: Very productive.
Regularity of bearing: Regular.
Trunk:
- *Diameter in relation to length.*—Stocky.
- *Surface characteristics.*—Medium.

Branches:
- *Size.*—Medium.
- *Surface character.*—Medium.
- *Color.*—Montella (Plate 8-J-11).
- *Lenticels.*—Number — numerous; size — 0.75 mm×5 mm.

Leaves:
- *Size.*—Large.
- *Length.*—170 mm.
- *Width.*—45 mm.
- *Shape.*—Oval, lanceolate.
- *Color.*—Upperside — Privet (Plate 24-J-6); Lowerside — Cedar Green (Plate 23-H-6).
- *Marginal form.*—Finely serrate.
- *Petiole.*—Length — 12 mm; Thickness — 2 mm.
- *Stem glands.*—Number — 1 to 3. Arrangement — Variable. Size — 0.3 mm×0.5 mm. Type — Reniform. Color — Gold.

Flower buds:
- *Size.*—Medium to large.
- Shape.—Obtuse-conical and plump.
- *Surface.*—Pubescent.

Flowers:

*Dates of bloom in 1983.*—Pink bud, Feb. 14; first bloom, Feb. 16; 25% of bloom complete, Feb. 21; full bloom, Feb. 25.

*Size.*—Large.

*Color.*—Upperside — Sweet briar (Plate 1-D-4). Lowerside — Sweet briar (Plate 1-E-4).

*Number of pistils and stamens.*—Pistils — 1; Stamen — 36 to 44.

FRUIT

Maturity: Met minimum maturity standards in Arvin, Calif. on June 1, 1983.

Size:

*Uniformity.*—Uniform

*Diameter.*—59 to 71 mm.

*Transverse in suture plane.*—56 to 68 mm.

*Transverse at right angles to suture plane.*—58 to 68 mm.

Form:

*Uniformity.*—Uniform.

*Symmetry.*—Round-oblong with equal sides.

*Suture.*—Distinct, deep, extending from base to pistil point.

*Ventral surface.*—Lipped throughout.

*Stem cavity.*—Acute, 15 mm×20 mm×10 mm deep.

*Base.*—Shoulders rounded.

*Apex.*—Cuspidate.

*Pistil point.*—Apical.

*Stem.*—Length — 8 mm; caliper — 3 mm.

*Skin.*—Thickness — Medium; Texture — Medium; Tendency to Crack — None; Color — Ground color: Doubloom to Roman Ochre (Plate 11-K-10); Blush — Maroon (Plate 7-L-7); Pubescence — None.

Flesh:

*Color.*—Spanish Yellow (Plate 10-L-7).

*Color of pit well.*—Honey Sweet (Plate 11-J-6).

*Juice.*—Juicy.

*Flavor.*—Pleasant, subacid.

*Aroma.*—Pleasant.

*Texture.*—Firm, meaty.

*Fibers.*—Abundant, coarse and tough.

*Ripening.*—Even.

Eating quality: Good.

Stone: Semi-free, with some flesh adhering on both sutures.

*Size.*—Large, 40 mm long, 26 mm breadth, 20 mm thick,

*Form.*—Oblong; cuneate towards apex.

*Sutures.*—Ventral — Narrow and shallowly grooved. Dorsal — Wide with shallow groove throughout.

*Base.*—Straight.

*Sides.*—Irregularly furrowed near apex, pitted toward base.

*Color.*—Cork (Plate 12-B-7).

*Splitting tendency.*—Slight.

Use: Fresh market.

Keeping quality: Good.

Shipping quality: Good.

Although the new variety of nectarine tree possesses the described characteristics as a result of the growing conditions in Fresno County, Calif., in the central part of the San Joaquin Valley, it is to be understood that variations of the usual magnitude in characteristics incident to growing conditions, fertilization, pruning and pest control are to be expected.

Having thus described and illustrated our new variety of Nectarine Tree, what is new and desired to be secured by Letters Patent is:

1. A new and distinct variety of nectarine tree substantially as illustrated and described broadly characterized by its general similarity to the May Grand Nectarine Tree (U.S. Plant Pat. No. 2,794) in its early bearing of fruit having yellow flesh but from which it is distinguished as to novelty by its regular and very productive bearing of fruit having a more completely yellow flesh and a somewhat flatter appearance, ripening two or three days earlier than that of the May Grand variety.

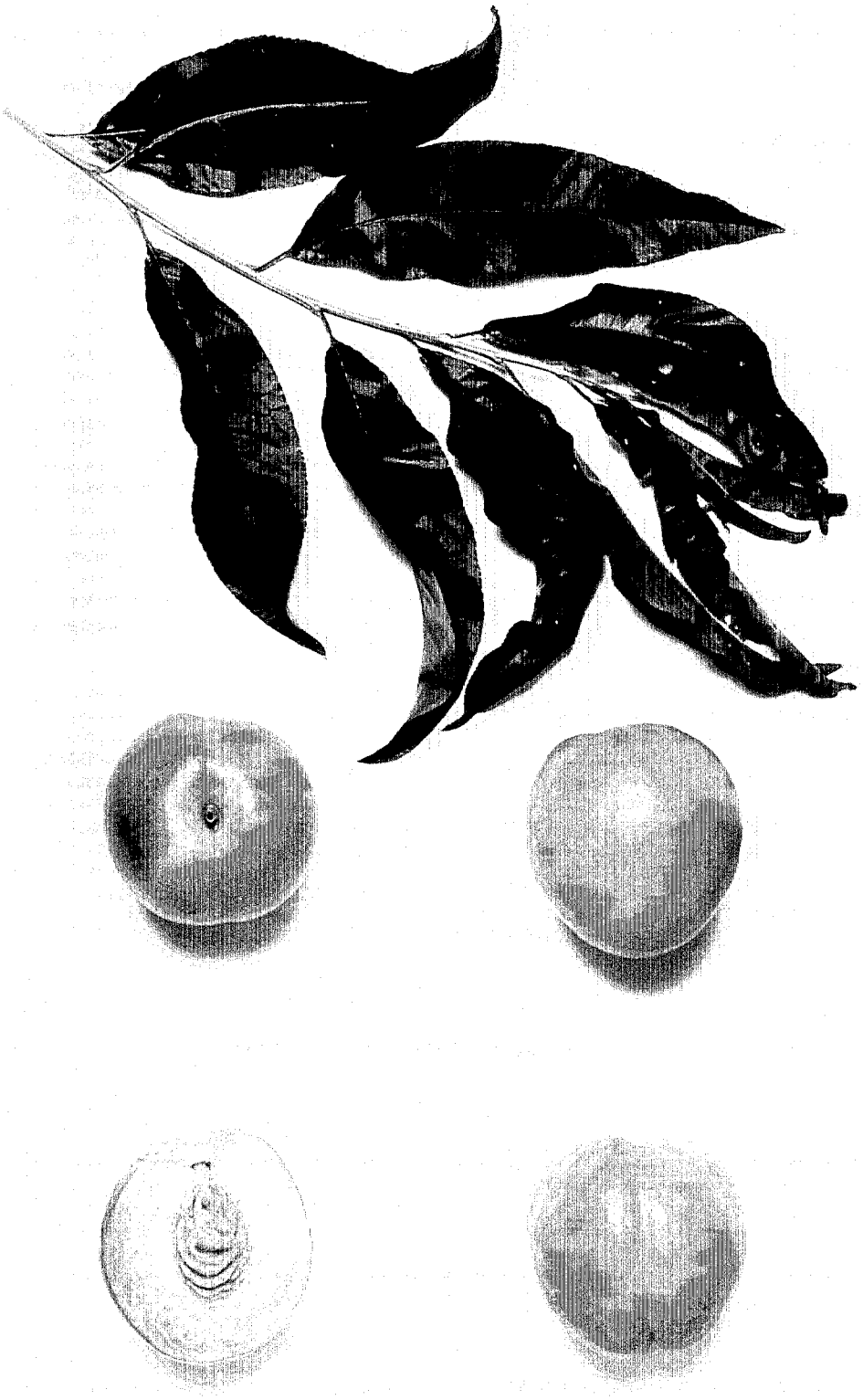

* * * * *